(12) United States Patent
Crespo et al.

(10) Patent No.: US 12,262,760 B1
(45) Date of Patent: Apr. 1, 2025

(54) UNDERWEAR GARMENT SYSTEM FOR INCONTINENCE, UROLOGICAL AND INTESTINAL CONDITIONS

(71) Applicants: Maria Teresa Crespo, Coral Gables, FL (US); Isabella Duarte-Crespo, Coral Gables, FL (US)

(72) Inventors: Maria Teresa Crespo, Coral Gables, FL (US); Isabella Duarte-Crespo, Coral Gables, FL (US)

( * ) Notice: Subject to any disclaimer, the term of this patent is extended or adjusted under 35 U.S.C. 154(b) by 5 days.

(21) Appl. No.: 18/083,663

(22) Filed: Dec. 19, 2022

Related U.S. Application Data

(63) Continuation-in-part of application No. 15/898,681, filed on Feb. 19, 2018, now abandoned.

(51) Int. Cl.
*A41B 9/14* (2006.01)
*A41D 15/00* (2006.01)
*A41D 15/04* (2006.01)

(52) U.S. Cl.
CPC .............. *A41B 9/14* (2013.01); *A41D 15/00* (2013.01); *A41D 15/005* (2013.01); *A41D 15/04* (2013.01); *A41D 2300/332* (2013.01); *A41D 2400/42* (2013.01); *A41D 2400/422* (2013.01)

(58) Field of Classification Search
CPC ........ A41B 9/14; A41D 15/00; A41D 15/005; A41D 15/04; A41D 2300/332; A41D 2400/42; A41D 2400/422
See application file for complete search history.

(56) References Cited

U.S. PATENT DOCUMENTS

| | | | | |
|---|---|---|---|---|
| 2,072,030 A | * | 2/1937 | Damron ................ | A41D 27/20 2/87 |
| 2,544,840 A | * | 3/1951 | Kowatsch ............. | A41D 7/005 2/67 |
| 3,085,254 A | * | 4/1963 | Cutler ................... | A41D 27/20 2/243.1 |
| 3,137,862 A | * | 6/1964 | Mizerak ................ | A41D 27/20 2/400 |
| 4,145,762 A | * | 3/1979 | Wallach ................ | A41D 7/005 2/238 |
| 4,502,154 A | * | 3/1985 | Itoi ....................... | A41D 15/04 2/108 |
| D283,077 S | * | 3/1986 | Crandall ............... | D2/738 |

(Continued)

*Primary Examiner* — Khaled Annis
(74) *Attorney, Agent, or Firm* — John Rizvi; John Rizvi, P.A.—The Patent Professor®

(57) ABSTRACT

An underwear garment system may include a main underwear garment, including a wearable body portion having an inner side facing the wearer. A first pocket and a second pocket, each having a top opening, may be carried by the body portion on the inner side, concealed from sight. The second pocket may be formed of a fluid impermeable material and may be suspended from the body portion in a pivotable manner with respect to the body portion. The body portion may be deformable and pivoted about the pivot point to fit within the second pocket. The main underwear garment may be configured to selectively adopt a wearable, first configuration and storage or second configuration. In the second configuration, the body portion may be deformed, pivoted, and fluid-tightly received within the second pocket. A compressed, elastic strip may retain the body portion within the second pocket in the second configuration.

19 Claims, 8 Drawing Sheets

(56) References Cited

U.S. PATENT DOCUMENTS

| | | | | |
|---|---|---|---|---|
| 5,172,430 | A * | 12/1992 | Lerma-Solis | A41B 9/02 2/403 |
| D339,219 | S * | 9/1993 | Beauchemin | D2/713 |
| D382,386 | S * | 8/1997 | Malone | D2/731 |
| 5,850,634 | A * | 12/1998 | Toombs | A41D 15/04 2/93 |
| 6,018,823 | A * | 2/2000 | Ortmeier | A41D 27/20 450/150 |
| 6,076,195 | A * | 6/2000 | Klein | A41B 9/023 2/403 |
| 6,308,340 | B1 | 10/2001 | Cook | |
| 6,772,446 | B1 * | 8/2004 | Black | A41B 9/04 2/400 |
| 6,817,031 | B1 * | 11/2004 | Gravlin | A41D 15/04 2/250 |
| 7,231,672 | B2 * | 6/2007 | Thomas | A41B 9/02 2/400 |
| D672,529 | S * | 12/2012 | Lucas | D2/716 |
| D775,782 | S | 1/2017 | Peete | |
| 9,936,746 | B1 * | 4/2018 | Park | A63H 3/02 |
| 10,674,777 | B2 * | 6/2020 | Fisher | A41D 27/204 |
| 11,246,361 | B1 * | 2/2022 | Wimer-Golebiowski | A41D 1/22 |
| 2004/0083538 | A1 * | 5/2004 | Thomas | A41D 27/201 2/400 |
| 2005/0081275 | A1 * | 4/2005 | Galvao | A41D 7/005 2/67 |
| 2005/0137548 | A1 * | 6/2005 | Riley | A61F 13/8405 604/385.01 |
| 2006/0101558 | A1 * | 5/2006 | Coleman | A61F 13/84 2/400 |
| 2007/0083985 | A1 * | 4/2007 | Nathan | A41B 9/001 2/400 |
| 2008/0010716 | A1 * | 1/2008 | Brown | A41D 13/1254 2/78.1 |
| 2008/0109945 | A1 * | 5/2008 | Xia | A41B 9/023 2/403 |
| 2008/0189832 | A1 * | 8/2008 | Oscher | A41D 7/005 2/400 |
| 2008/0196147 | A1 * | 8/2008 | Kume | A41B 9/04 2/250 |
| 2010/0281595 | A1 * | 11/2010 | Gernes | A41B 9/001 2/69 |
| 2012/0311758 | A1 | 12/2012 | Nicholson | |
| 2013/0067631 | A1 * | 3/2013 | Crye | A41D 3/00 2/85 |
| 2014/0047620 | A1 * | 2/2014 | Ingalls | A41B 9/02 2/403 |
| 2014/0090147 | A1 * | 4/2014 | Tyler | A45C 9/00 2/69 |
| 2014/0259306 | A1 | 9/2014 | Shinn | |
| 2015/0026869 | A1 * | 1/2015 | Groceman | A41D 27/20 2/400 |
| 2015/0359273 | A1 | 12/2015 | Olson | |
| 2018/0153229 | A1 * | 6/2018 | Virgilio | A41D 1/02 |
| 2018/0368482 | A1 * | 12/2018 | Chea | A41B 9/04 |
| 2019/0150521 | A1 * | 5/2019 | Pai | A41B 9/04 |
| 2019/0254369 | A1 * | 8/2019 | Crespo | A41D 27/208 |
| 2019/0350277 | A1 * | 11/2019 | Mahoney | A41D 3/04 |
| 2020/0093245 | A1 * | 3/2020 | Romano | A41D 27/20 |
| 2020/0214373 | A1 * | 7/2020 | Wade | A41D 15/04 |
| 2022/0378113 | A1 * | 12/2022 | Frautten | A41B 9/023 |

\* cited by examiner

UNDERWEAR GARMENT SYSTEM FOR INCONTINENCE, UROLOGICAL AND INTESTINAL CONDITIONS

CROSS-REFERENCE TO RELATED APPLICATIONS

This application is a Continuation-In-Part of U.S. patent application Ser. No. 15/898,681, filed on Feb. 19, 2018, which is incorporated by reference herein in its entirety.

FIELD OF THE INVENTION

The present invention relates generally to underwear garments, and more particularly, to an underwear garment which contains effectively concealed and secured pockets, including a personal item storage pocket for carrying medical supplies, personal items, etc., and an impermeable pocket providing an easy and effective means of storing soiled underwear. The pockets may also provide for the storage of a clean replacement underwear.

BACKGROUND OF THE INVENTION

People suffering from a variety of health conditions, such as incontinence, multiple sclerosis, certain intestinal conditions (e.g., inflammatory bowel disease), etc. may experience urinary or intestinal undesired events while outside their home. Often, upon an occurrence of such an undesired event, these individuals may not be able to return home and may need to change their underwear on the go. To prepare for such an event, these individuals typically carry a clean replacement underwear in their backpack, purse, or other personal item storage bag.

In the event of a urinary or intestinal accident, the individual must discreetly, and sometimes rapidly, remove their soiled underwear, store the soiled underwear in a plastic bag or elsewhere, place the plastic bag containing the soiled underwear in their backpack or other storage bag, extract the clean replacement underwear from their storage bag, and fit on the clean underwear. Some individuals, such as children, may be overwhelmed by this process and may misplace the soiled underwear during the process, which may cause frustration and stress. In fact, younger children may require the help of an adult such as a parent, teacher, or caregiver to carry out this process safely, hygienically, and discreetly. However, an adult may not always be readily available, and the child may need to remain wearing the soiled underwear until help arrives, leading to increased stress and potential embarrassment for the child.

The present invention aims to solve at least one of the aforementioned problems. For example, a solution is sought which reduces an individual's stress levels in the event of an undesired urinary or intestinal accident, by facilitating replacing a soiled underwear garment with a clean underwear garment, and discreetly and hygienically storing the soiled garment.

SUMMARY OF THE INVENTION

The present invention is directed to an underwear garment which contains effectively concealed and secured pockets, including a personal item storage pocket for carrying medical supplies, personal items, etc., and an impermeable pocket providing an easy and effective means of storing soiled underwear. The pockets may also provide for the storage of a clean replacement underwear. In this way, the invention provides a novel, unique, holistic, sustainable, and non-invasive remedy for people suffering from urological (incontinence, MS, etc.), intestinal conditions (i.e. Crohn's disease, etc.), or other medical conditions to store their medications, medical supplies, clean replacement underwear and soiled underwear, in a discreet, hygienic, and helpful manner.

In a first implementation of the invention, an underwear garment system may include a main underwear garment. The main underwear garment may include a body portion configured to be worn about a trunk of a wearer, predominantly below a waist of the wearer and along a crotch area of the wearer. The body portion may include an inner side configured to face the wearer. The main underwear garment may further include a first pocket and a second pocket carried by the body portion on the inner side thereof. The first pocket and second pocket may each include a respective top opening providing access to a respective interior space. The second pocket may be formed of a fluid impermeable material and may be suspended from the body portion such that a connection between the second pocket and body portion defines a pivot point. The body portion may be deformable and pivotable about the pivot point to fit within the interior space of the second pocket. The main underwear garment may be configured to selectively adopt a first configuration and a second configuration. In the first configuration, the body portion may be deployed and worn by the wearer, and the first and second pockets may be arranged on the inner side of the body portion and concealed from an outside observer. In the second configuration, the body portion may be deformed to fit within the interior space of the second pocket, and may be pivoted about the pivot point and received within the interior space of the second pocket. Also in the second configuration, the second pocket may prevent a fluid emanating from the body portion from leaking out of the interior space of the second pocket.

In a second aspect, the main underwear garment may include a waistband at a top edge of the body portion.

In another aspect the opening of the first pocket may be arranged adjacent to the waistband.

In another aspect, the opening of the first pocket may be arranged at a bottom edge of the waistband.

In another aspect, the opening of the second pocket may be arranged adjacent to the waistband.

In yet another aspect, the opening of the second pocket may be arranged at a bottom edge of the waistband.

In another aspect, the openings of the first and second pockets may be arranged adjacent to the waistband.

In another aspect, the openings of the first and second pockets may be arranged at a bottom edge of the waistband.

In another aspect, the first and second pockets may be elongated along a left-to-right direction of the underwear garment.

In yet another aspect, the first pocket, top opening of the first pocket, and interior space of the first pocket may be defined by and between the inner side of the body portion and a panel attached to the inner side of the body portion.

In another aspect, the second pocket may be defined by first and second panels extending from one another at a bottom edge and opposite side edges. The top opening of the second pocket may be defined by and between respective top edges of the first and second panels.

In another aspect, the second pocket may include an elastic strip at the top opening of the second pocket. In the second configuration of the main underwear garment, the elastic strip may be compressed to thereby retain the body portion within the interior space of the second pocket.

In another aspect, the elastic strip may surround the top opening of the second pocket in its entirety.

In yet another aspect, in the first configuration of the main underwear garment, the elastic strip may be stretched and tensioned.

In another aspect, the underwear garment system may further include a second underwear garment. The second underwear garment may be deformable and fittable through the top opening of the first pocket and within the interior space of the first pocket. In some embodiments, the second underwear garment may be made of a single fabric layer.

In another aspect, the underwear garment system may further include a second underwear garment. The second underwear garment may be deformable and fittable through the top opening of the second pocket and within the interior space of the first pocket. In some embodiments, the second underwear garment may be made of a single fabric layer.

In another aspect, at least one of the first and second pockets may be non-detachably attached to the body portion.

In another aspect, the underwear garment system may further include at least one of a pad and a liner received in at least one of the first pocket and the second pocket.

In yet another aspect, the underwear garment system may further include at least one portable catheter received in at least one of the first pocket and the second pocket.

In another aspect, the underwear garment system may further include at least one wipe received in at least one of the first pocket and the second pocket.

These and other objects, features, and advantages of the present invention will become more readily apparent from the attached drawings and the detailed description of the preferred embodiments, which follow.

BRIEF DESCRIPTION OF THE DRAWINGS

The preferred embodiments of the invention will hereinafter be described in conjunction with the appended drawings provided to illustrate and not to limit the invention, where like designations denote like elements, and in which.

Like reference numerals refer to like parts throughout the several views of the drawings.

DETAILED DESCRIPTION

The following detailed description is merely exemplary in nature and is not intended to limit the described embodiments or the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to make or use the embodiments of the disclosure and are not intended to limit the scope of the disclosure, which is defined by the claims. For purposes of description herein, the terms "upper", "lower", "left", "rear", "right", "front", "vertical", "horizontal", and derivatives thereof shall relate to the invention as oriented in FIG. 1. Furthermore, there is no intention to be bound by any expressed or implied theory presented in the preceding technical field, background, brief summary or the following detailed description. It is also to be understood that the specific devices and processes illustrated in the attached drawings, and described in the following specification, are simply exemplary embodiments of the inventive concepts defined in the appended claims. Hence, specific dimensions and other physical characteristics relating to the embodiments disclosed herein are not to be considered as limiting, unless the claims expressly state otherwise.

The present invention is directed toward an underwear garment which contains effectively concealed and secured pockets, including a personal item storage pocket for carrying medical supplies, personal items, etc., and an impermeable pocket providing an easy and effective means of storing soiled underwear. The pockets may also provide for the storage of a clean replacement underwear.

Figure 1:
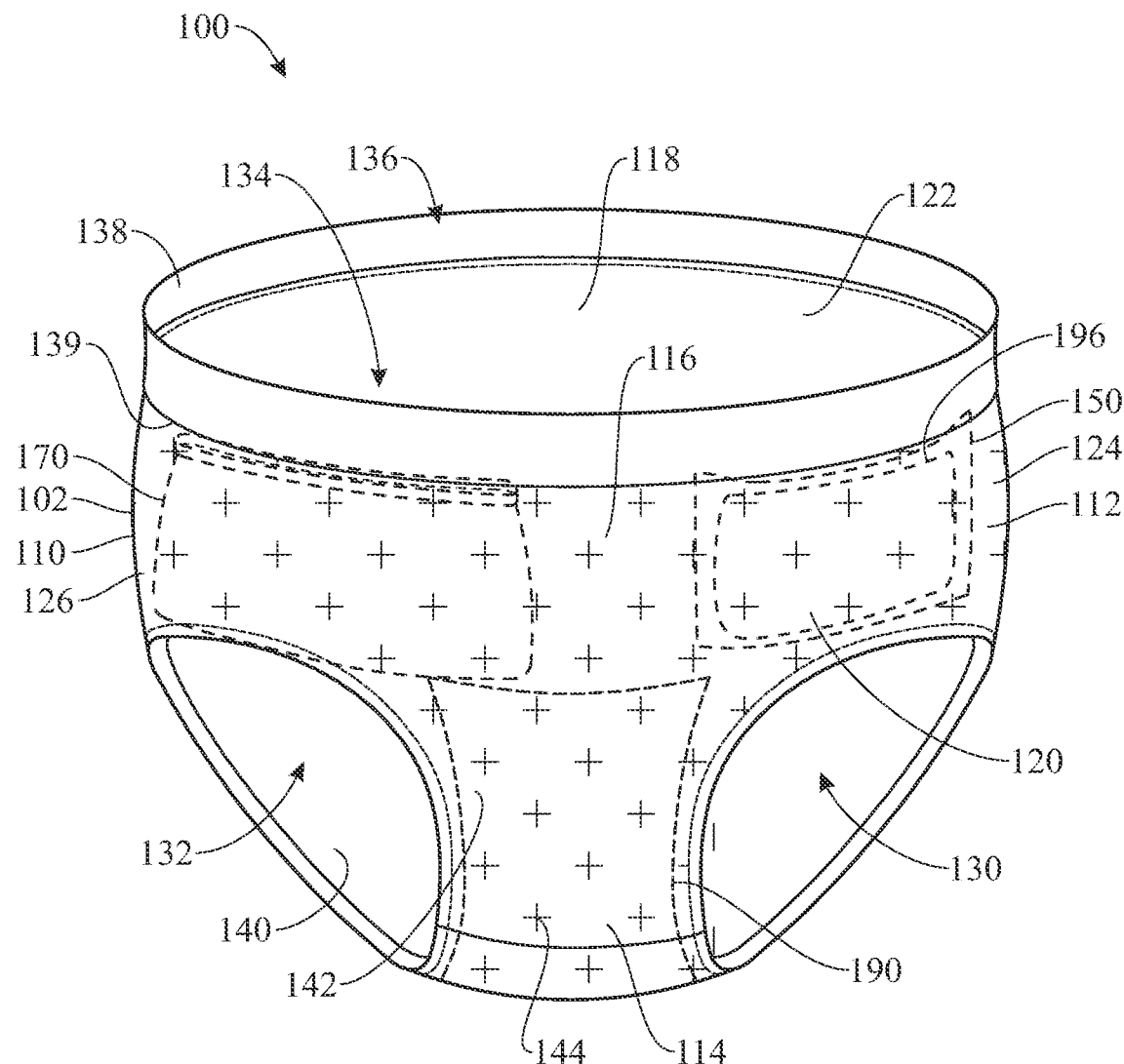
FIG. 1 presents a front view of an underwear garment system in accordance with a first embodiment of the present invention, including a main underwear garment having internal first and second pockets, and a second underwear garment shown folded and stored within the first pocket.
Figure 2:
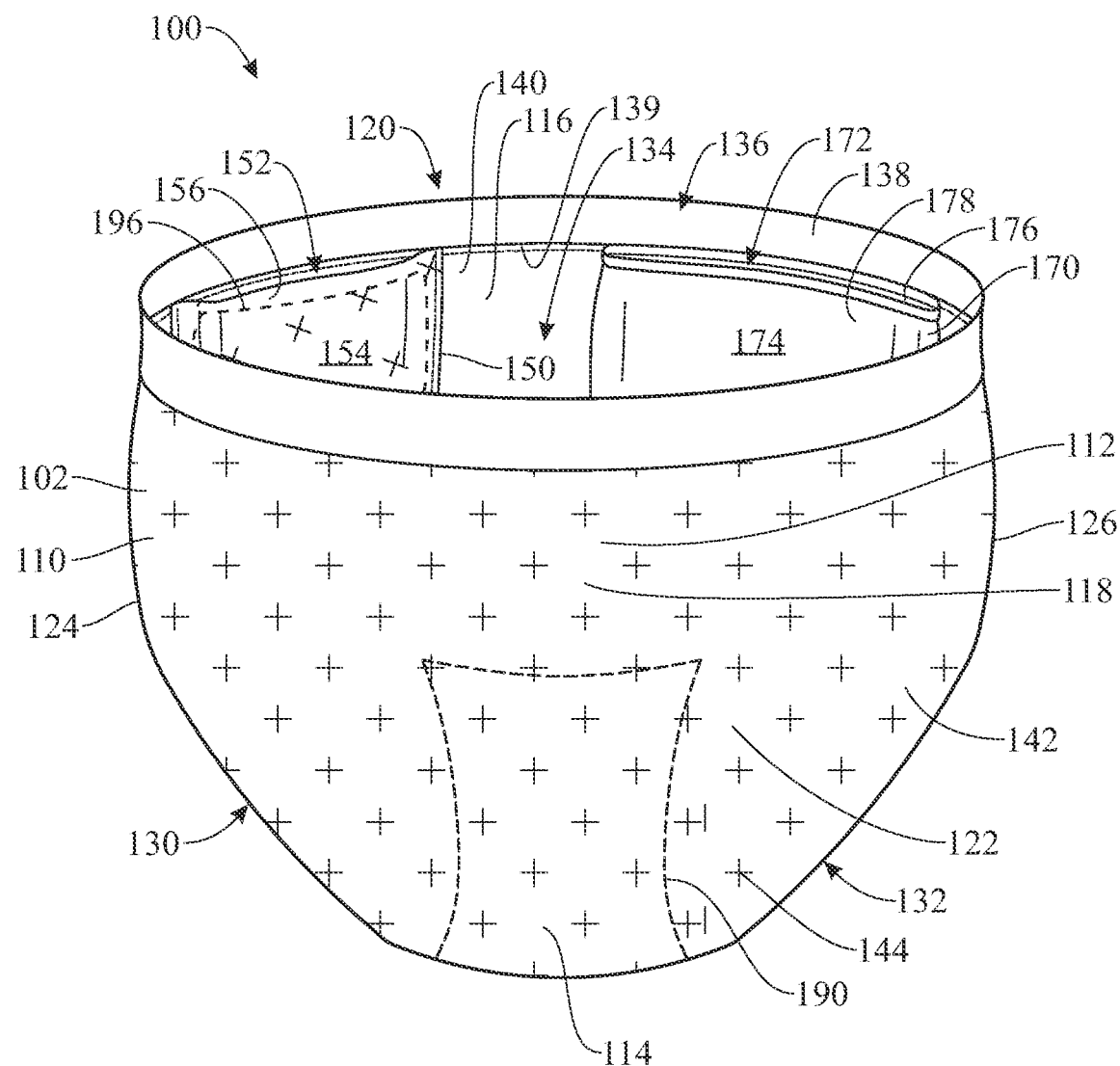
FIG. 2 presents a rear view of the underwear garment system of FIG. 1.

Referring initially to FIGS. 1 and 2, an underwear garment system 100 is shown in accordance with an illustrative embodiment of the present invention. The underwear garment system 100 includes a main underwear garment 102, which is modifiable from underwear to bag and bag to underwear, as will be described in more detail hereinbelow. The main underwear garment 102 includes a main underwear body, hereinafter referred to as body portion 110, which is wearable by a user about the user's crotch area. The body portion 110 may include a top portion 112, configured to wrap around the user's body, and a crotch portion 114 affixed to the top portion 112 and configured to extend along the user's crotch area. The crotch portion 114 may extend from a central section 116 of the top portion 112 at a front side 120 of the body portion 110, as shown in FIG. 1, to a central section 118 of the top portion 112 at a rear side 122 of the body portion 110, as shown in FIG. 2. It should be noted that the design (e.g., height, width, shape, etc.) of the top portion 112 and crotch portion 114 may vary without departing from the scope of the present disclosure. As best shown in FIG. 1, a first leg opening 130 may be defined between the top portion 112 and crotch portion 114 on a right side 124 of the body portion 110, and a second leg opening 132 may be defined between the top portion 112 and crotch portion 114 on a left side 126 of the body portion 110. The first and second leg openings 130 and 132 may be separated from one another by the crotch portion 114.

The body portion 110 may be formed of one or more fabric and/or other applicable materials, and may be constructed in a single-piece or single-panel configuration or instead include multiple panels attached to one another, such as by stitching, welding, etc. The panel or panels may each be formed by one or more layers of said fabric and/or other applicable materials.

As further shown in FIGS. 1 and 2, the body portion 110 may define an interior space 134 configured to receive the wearer's body. The body portion 110 may terminate in a top opening 136. The top opening 136 and first and second leg openings 130 and 132 may be in spatial communication with the interior space 134. in some embodiments, a waistband 138 may extend along the top edge of the body portion 110, about the top opening 136. The waistband 138 may be elastically stretchable, to provide a relatively tight yet comfortable fit against the wearer's body. An inner side 140 of the body portion 110 may face the interior space 134 and may be configured to contact the wearer's skin, while an outer side 142 of the body portion 110 may be arranged opposite the inner side 140 and interior space 134, and face outward relative to the wearer's body. In some embodiments, the outer side 142 may include one or more decorative elements 144, such as, but not limited to, a pattern, texture, color, etc.

With continued reference to FIG. 1, a first pocket 150 and a second pocket 170 may be carried by the body portion 110 on the inner side 140 thereof. The first pocket 150 and second pocket 170 may be concealed from sight when a user is wearing the main underwear garment 102, allowing the external appearance of the main underwear garment 102 to be that of a conventional underwear. In some embodiments, as shown, the first and second pockets 150 and 170 may be arranged on the front side 120 of the main underwear garment 102, generally above the first leg opening 130 and second leg opening 132, respectively. However, alternative embodiments are contemplated without departing from the scope of the present disclosure; in a non-limiting example, one of the first and second pockets 150 and 170 may be located on the rear side 122 of the main underwear garment 102.

In preferred embodiments, at least one, and preferably both of the first and second pockets 150 and 170 may be elongately formed in a left-to-right, transverse direction; i.e., may have a width which is greater than the corresponding height. For example, the first and second pockets 150 and 170 shown herein are generally rectangular, having a relatively large width (relative to their respective height). Having transversely elongated first and/or second pockets 150 and 170 allows to maximize the volume of the respective interior spaces 154, 174, even in smaller-sized or low-waist underwear garments 102.

The first pocket 150 may include a top opening 152 allowing access to an interior space 154 of the first pocket 150. In turn, the second pocket 170 may include a top opening 172 allowing access to an interior space 174 of the second pocket 170. The interior space 154 of the first pockets 150 may be separated, i.e. not communicated with, the interior space 174 of the second pocket 170. In some embodiments, such as the present embodiment, the first and second pockets 150 and 170 may be spaced-apart from one another. In some embodiments, the top opening 152 and/or top opening 172 may be arranged generally parallel to a top edge of the main underwear garment 102 (e.g., generally parallel to the waistband 138). In some embodiments, the top opening 152 and/or top opening 172 may be positioned near the top opening 136 of the body portion 110; for example, the top openings 152 and 172 of the present embodiment are positioned immediately below the waistband 138, on the inner side 140 of the body portion 110.

Figure 3:
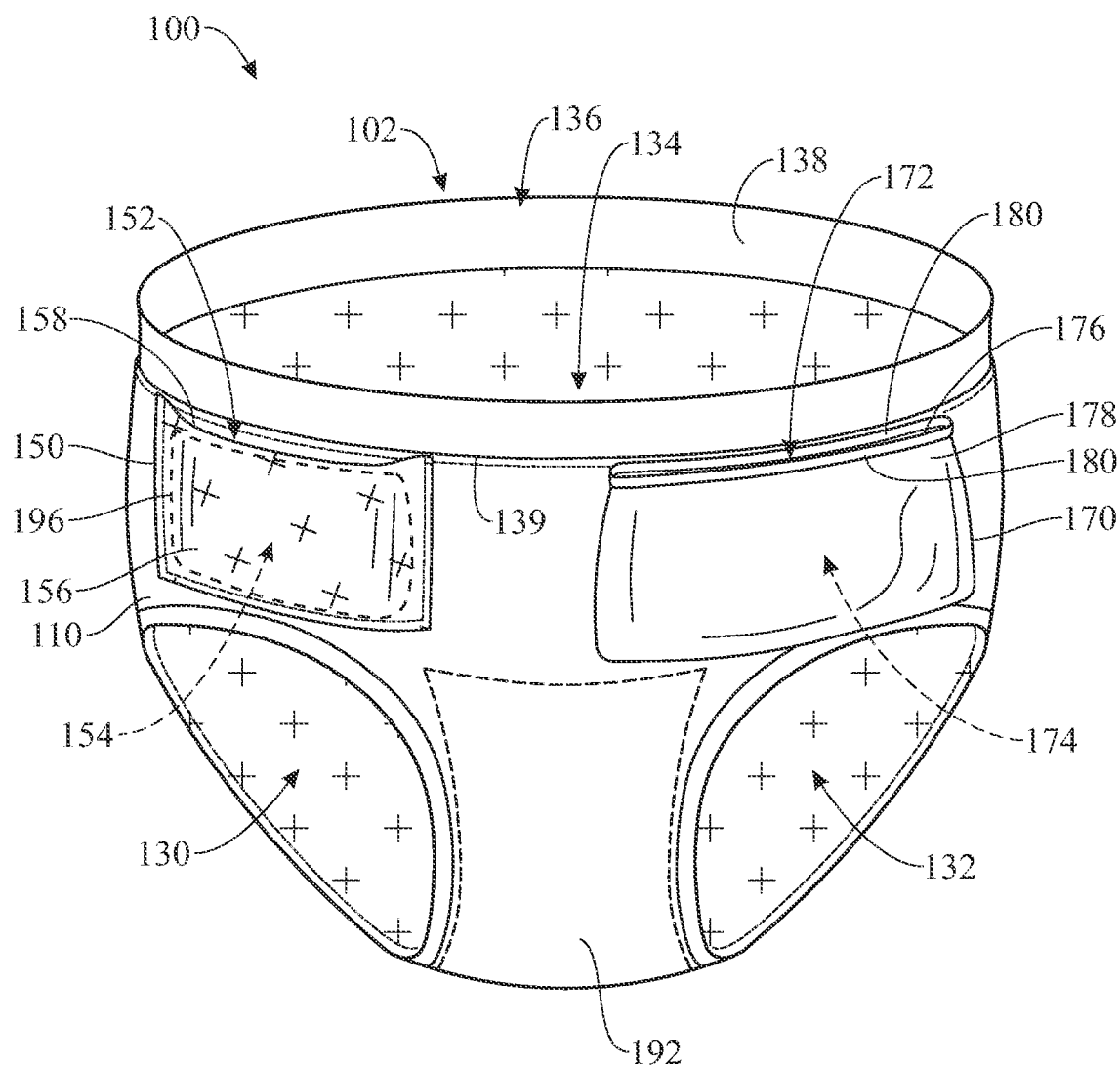
FIG. 3 presents a front view of the underwear garment system of FIG. 1, with the main underwear garment flipped inside out.

With reference now to FIGS. 2 and 3, in some embodiments, the first pocket 150 may be defined by a wall or panel 156 arranged on the inside of the main underwear garment 102. In preferred embodiments, such as the present embodiment, the panel 156 is affixed to the body portion 110 at the inner side 140 of the body portion 110, such that the interior space 154 of the first pocket 150 is defined by and between the inner side 140 of the body portion 110 and the panel 156. The panel 156 may be attached to the inner side 140 of the body portion 110 such as by stitching, welding, or other applicable means. In some embodiments, the panel 156 may be attached to the inner side 140 along a full perimeter of the panel 156 except for a top edge 158 of the panel 156; the top edge 158 of the panel 156 may be detached from the inner side 140 of the body portion 110 to define the top opening 152 of the first pocket 150.

In some embodiments, the first pocket 150 may include one or more fasteners at the top opening 152 to selectively open and at least partially close the top opening 172 to retain one or more items within the interior space 154 of the first pocket 150. In other embodiments, such as the present embodiment, the top opening 152 may be permanently open, and items stored within the interior space 154 may be retained therein by the wearer's body pressing against the first pocket 150 and flattening the panel 156 against the body portion 110 of the main underwear garment 102.

In preferred embodiments, the panel 156 may be made of a same material and number of layers as the body portion 110. For instance, the body portion 110 and panel 156 may each be made of a single layer of the same fabric material and construction (e.g., threaded cotton), optionally including the same decorative elements 144 as shown.

Figure 4:
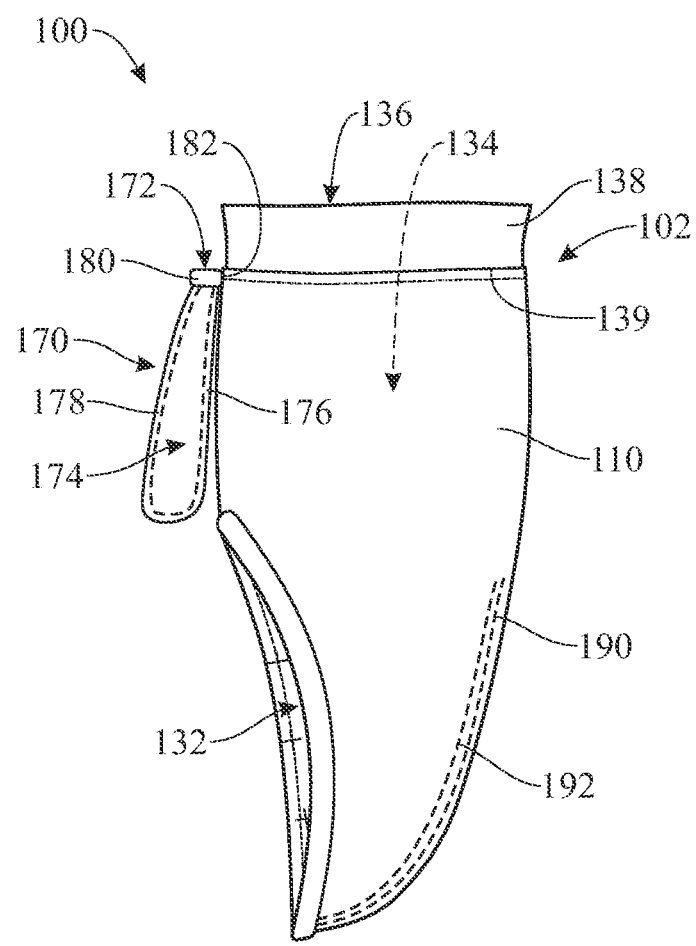
FIG. 4 presents a right side view of the main underwear garment of FIG. 3.

With continued reference FIGS. 2-4, in some embodiments, contrary to the first pocket 150, the second pocket 170 is not defined by the inner side 140 of the body portion 110 and is instead defined by its own walls or panels. For example, in the present embodiment, the second pocket 170 has a generally flat construction and includes a first panel 176 and a second panel 178 arranged generally parallel to each other on the inside of the main underwear garment 102, with the first panel 176 arranged between the second panel 178 and the inner side 140 of the body portion 110 as best shown in FIG. 4. The first and second panels 176 and 178 may be connected to or otherwise extend from each other at a bottom edge and opposite side edges, and may be disconnected from each other at a top edge to define the top opening 172 of the second pocket 170. The interior space 174 of the second pocket 170 is defined by and between the first and second panels 176 and 178.

In some embodiments, the second pocket 170 may include one or more fasteners at the top opening 172 to selectively open and at least partially close the top opening 172 to retain one or more items within the interior space 174 of the second pocket 170. For instance, in the present embodiment, an elastic strip 180 is provided along the top edges of the first and second panels 176 and 178, about the top opening 172. The elastic strip 180 may be configured such that, when a wearer in accordance with the size of the main underwear garment 102 is wearing the main underwear garment 102, the second pocket 170 is generally flattened against the wearer's body and the elastic strip 180 is slightly stretched and tensioned and the top opening 172 has a first size. The elastic strip 180 may also be configured such that, when the main underwear garment 102 is instead removed from the wearer's body, the elastic strip 180 is relatively relaxed to a less stretched or non-stretched position, as a result of which the top opening 172 has a smaller, second size, for purposes that will be described hereinafter.

In preferred embodiments, the second pocket 170, and more specifically, the first and second panels 176 and 178 may be made of one or more layers of fabric and/or other applicable materials, of which at least one layer may be impermeable and configured to maintain fluids within the interior space 174 of the second pocket 170. I.e., in preferred embodiments, the walls or panels forming the first pocket 170 may be leakproof.

In some embodiments, the second pocket 170 may be detachably secured to the body portion 110 of the main underwear garment 102, such as by one or more of a hook-and-loop fastener, a snap fastener, a magnetic fastener, a zipper, or the like. In other embodiments, the second pocket 170 may be permanently attached to the body portion 110, such as by a stitching connecting a top end of the first panel 176 and/or the elastic strip 180 to the body portion 110. When permanently or detachably attached to the body portion 110, as best shown in FIG. 4, the second pocket 170 may be attached to the body portion 110 at a top end of the second pocket 170 and may be generally suspended from the body portion 110. The area at which the second pocket 170 and body portion 110 are attached to each other may generally define a pivot point 182 about which the body portion 110 may be flipped or pivoted for purposes that will be described hereinafter.

In some embodiments, as shown in FIGS. 1-4, at least one impermeable material 190 and at least one fluid-absorbent material 192 may be provided at the crotch portion 114. The at least one impermeable material 190 may be arranged outward of the at least one fluid-absorbent material 192, such that fluids emanated from the wearer's body are absorbed by the inner, at least one fluid-absorbent material 192 and are prevented from leaking out of the crotch area 114 by the at least one impermeable material 190.

Figure 5:
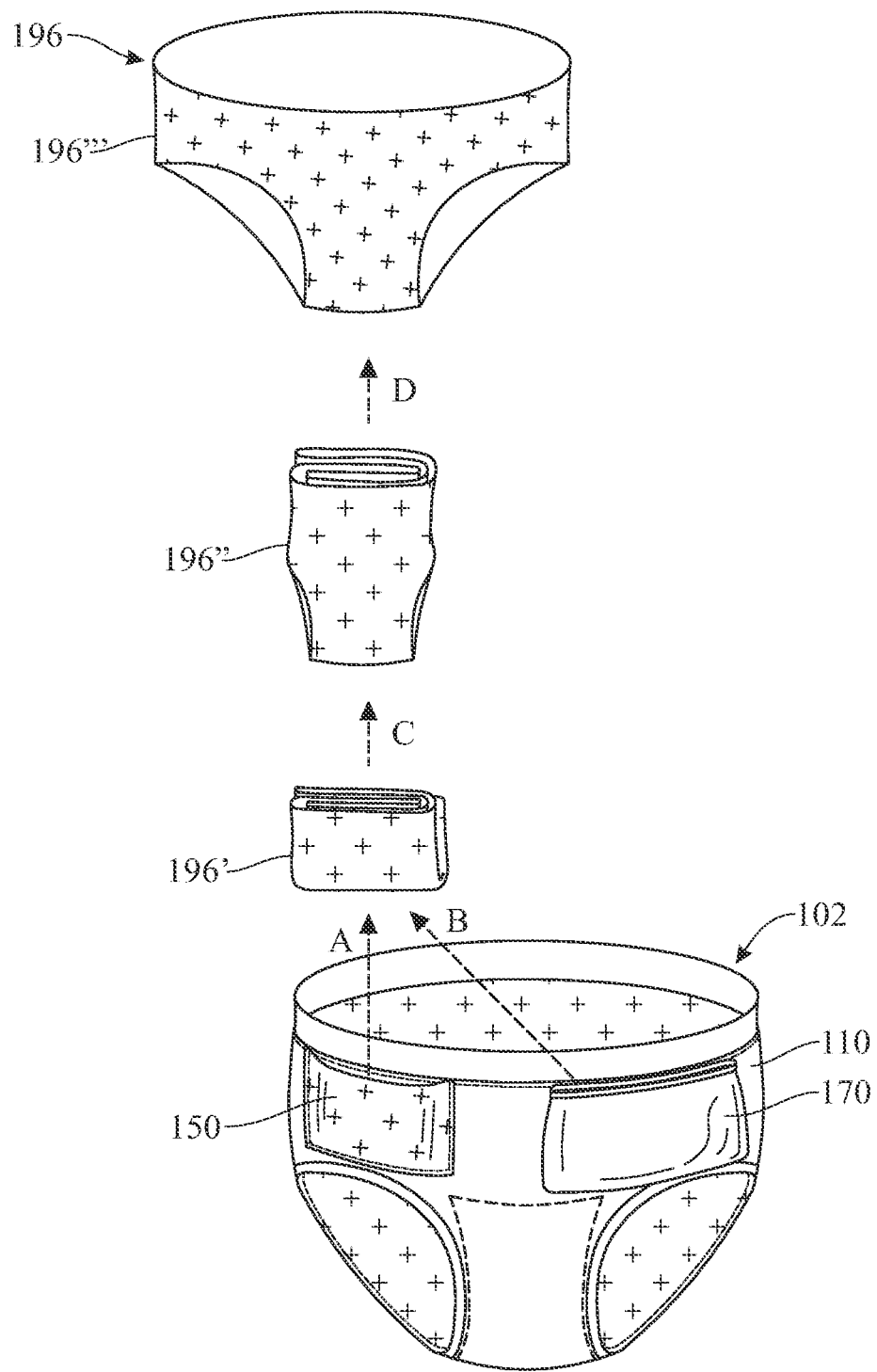
FIG. 5 presents a front view of the underwear garment system of FIG. 1, illustrating removal and deployment of the second underwear garment, in one step of an illustrative method of use of the underwear garment system.

In some embodiments, the underwear garment system 100 may further include a second underwear garment 196, an example of which is shown in FIG. 5. The second underwear garment 196 may be sized to be wearable by the same user of the main underwear garment 102, and may serve as a replacement undergarment as will be described in greater detail hereinafter. The second underwear garment may be initially folded or collapsed to a first configuration, indicated with reference numeral 196'. In some embodiments, in the folded or collapsed, first configuration, the second underwear garment 196' may fit entirely inside the first pocket 150, i.e. entirely within the interior space 154 of the first pocket 150; alternatively or additionally, in the folded or collapsed, first configuration, the second underwear garment 196' may fit entirely inside the second pocket 170, i.e. entirely within the interior space 174 of the second pocket 170. In preferred embodiments, the second underwear garment 196 may be lightweight, such as made of a single fabric layer, thereby minimizing bulkiness when stored in the first pocket 150, and the overall weight of the underwear garment system 100 and increasing user comfort when wearing the main underwear garment 102 with the second underwear garment 196 housed in the first pocket 150 or second pocket 170. In some embodiments, the second underwear garment 196 may have an outer appearance similar or the same as that of the main underwear garment 102, such as by including the same decorative elements 144; in addition to providing a pleasing visual effect, the similar or same outer appearance of the second underwear garment 196 may contribute to discreetness and privacy in situations where a user is required to replace the main underwear garment 102 with the second underwear garment 196 in the event that the main underwear garment 102 becomes soiled.

An illustrative method of operation of the underwear garment system 100 is now described with reference mainly to FIGS. 1 and 5-12. Initially, a user may fit on the main underwear garment 102. The user may choose to store the second underwear garment 196 in the folded or collapsed, first configuration inside the first pocket 150 or second pocket 170. For instance, the illustration of FIG. 1 shows the second underwear garment 196 initially folded and stored inside the first pocket 150. Alternatively, the second underwear garment 196 may be stored in the second pocket 170, and the first pocket 150 may instead be used to store medical supplies or items, personal items, or other applicable objects. Examples of items which may be safely and conveniently stored inside the first pocket 150 and/or second pocket 170 are medications, catheters, or wipes. In this initial configuration of FIG. 1, the first and second pockets 150 and 170 may be flattened, thereby minimizing their bulkiness, and may be concealed from sight by the main body 110. Furthermore, the elastic strip 180 of the second pocket 170 may be softly tensioned, thereby obtaining a flatter finish which contributes to concealment of the second pocket 170.

In the event of a urinary or intestinal accident, the underwear garment system 100 may assist the wearer in overcoming such an inconvenient situation in various ways. For example, in some embodiments, the impermeable material 190 comprised in the crotch portion 114 may at least partially prevent fluids from leaking out of the main underwear garment 102 through the crotch portion 114. Alternatively or preferably additionally, the fluid-absorbent material 192 comprised in the crotch portion 114 may absorb at least part of the fluids, contributing to reduce or prevent fluid leaks out of the main underwear garment 102. Additionally, the wearer or caregiver may choose to remove the soiled main underwear garment 102 and put on a clear, replacement undergarment.

For instance, in some applications, the wearer may carry the clean, replacement or second underwear garment 196 in the main underwear garment 102, as described heretofore, such that the second underwear garment 196 is readily available without the wearer or caregiver having to carry such a replacement underwear in a separate purse, backpack, or the like. The folded or collapsed, second underwear garment 196 may be initially stored, and thereafter removed from, the first pocket 150 or second pocket 170 as indicated in FIG. 5 by arrows A and B, respectively. To remove the underwear garment 196, the wearer or caregiver may simply insert their hand into the top opening 152 or 172 of the applicable first or second pocket 150, 170, which is facilitated by the top opening 152, 172 being adjacent to the top edge of the body portion 110 of the main underwear garment 102; in preferred embodiments, at least one of or, more preferably, both top openings 152, 172 are arranged generally at a bottom edge 139 of the waistband 138, i.e. immediately beneath the waistband 138. Once the second underwear garment 196 has been extracted from the first or second pocket 150, 170, the second underwear garment 196 may be unfolded or deployed from the initially folded or collapsed configuration (reference numeral 196'), to a partially-unfolded position (denoted with reference numeral 196") and further to a fully deployed position (denoted with reference numeral 196''').

With the replacement or second underwear garment 196 extracted from the main underwear garment 102, and the soiled main underwear garment 102 removed from the wearer's body, the wearer or caregiver may now discreetly and hygienically store the soiled main underwear garment 102 for later processing, such as for washing the main underwear garment 102 once the caregiver or wearer has arrived at their home, a medical facility, or other applicable destination. Specifically, the body portion 110 of the main underwear garment 102 may be folded or collapsed until the main underwear garment 102 may be fitted into the second pocket 170.

Figure 6:
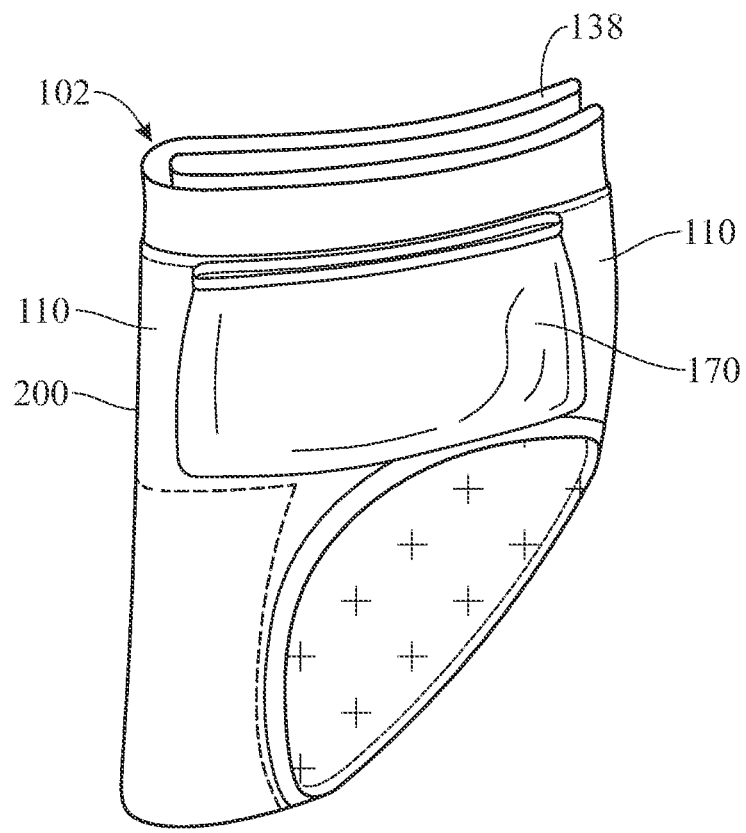
FIG. 6 presents a front view of the underwear garment system of FIG. 1, illustrating folding of the main underwear garment about a vertical fold line, in a further step of the illustrative method of use of the underwear garment system.
Figure 7:
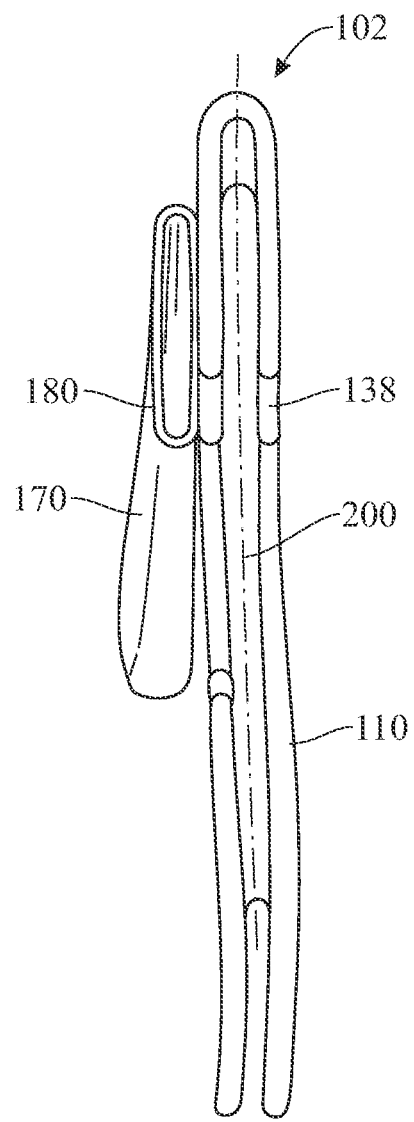
FIG. 7 presents a side view of the main underwear garment of FIG. 6.
Figure 8:
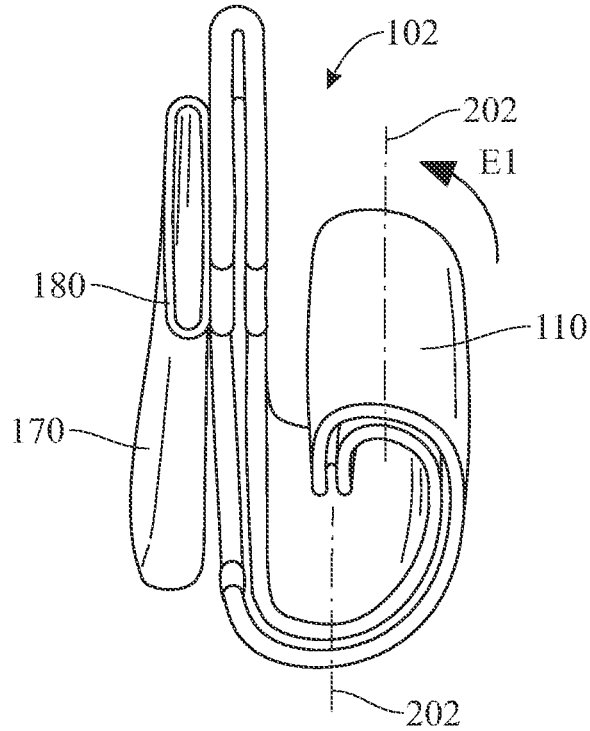
FIG. 8 presents a side view, similar to FIG. 7, illustrating folding or rolling of the main underwear garment, in a further step of the illustrative method of use of the underwear garment system.
Figure 9:
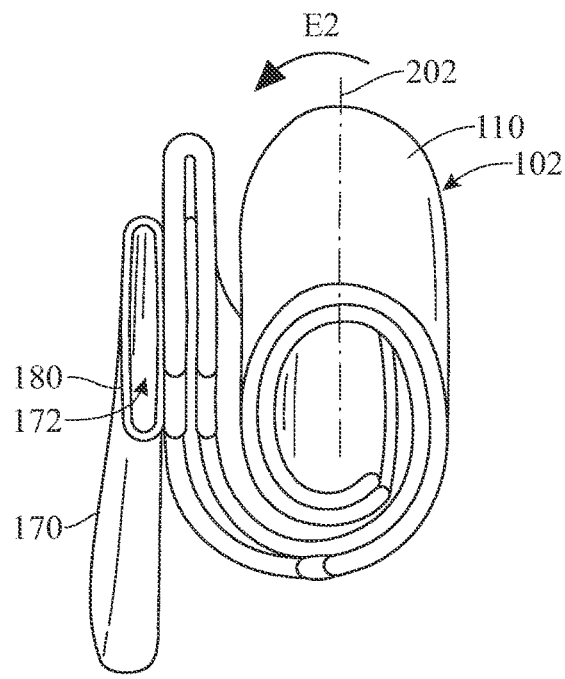
FIG. 9 presents a side view, similar to FIG. 8, illustrating further folding or rolling of the main underwear garment, in yet another step of the illustrative method of use of the underwear garment system.

For example, as shown in FIG. 6, the body portion 110 of the main underwear garment 102 may be folded about one or more generally vertical fold lines 200, until the width of the body portion 110 is adjusted to the available width of the interior space 174 of the second pocket 170. Next, as shown in FIGS. 7-9 and indicated by arrow E, the body portion 110 of the main underwear garment 102 may be folded along one or more generally horizontal fold lines 202, or otherwise rolled, bunched, or collapsed, until the resulting folded, rolled, bunched, or collapsed body portion 110 may be fitted inside the second pocket 170.

Figure 10:
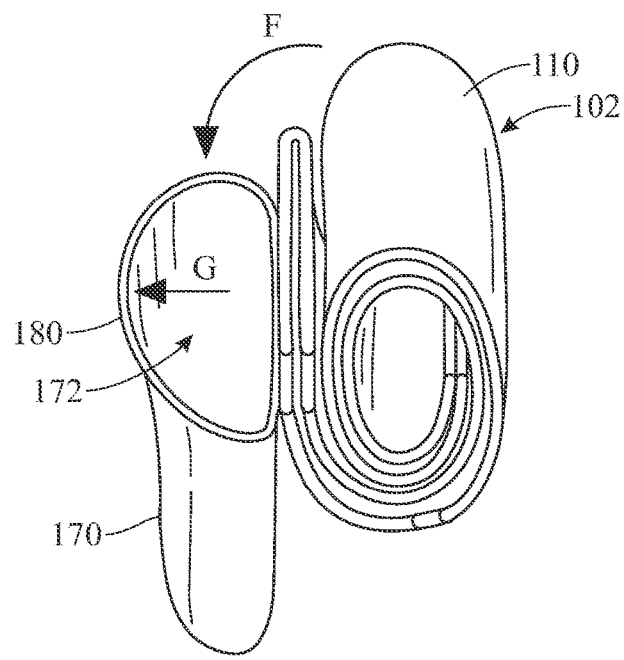
FIG. 10 presents a side view, similar to FIG. 9, illustrating a stretching out of the top opening of the second pocket and a flipping over of the folded or rolled, body portion of the main underwear garment, in a further step of the illustrative method of use of the underwear garment system.
Figure 11:
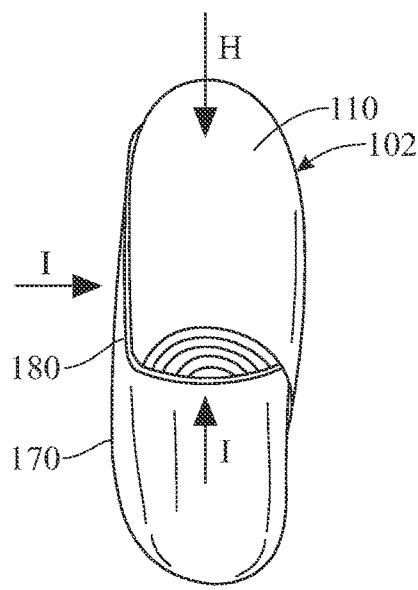
FIG. 11 presents a side view, similar to FIG. 10, illustrating the insertion of the folded or rolled, body portion of the main underwear garment into the second pocket, and the elastic adjustment of the elastic strip of the second pocket against the body portion, the second pocket fluid-tightly retaining the body portion of the main underwear garment therewithin.
Figure 12:
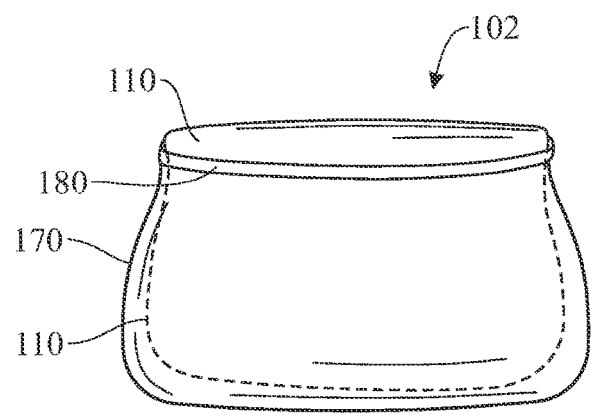
FIG. 12 presents a front view of the main underwear garment of FIG. 11.

Once the body portion 110 of the main underwear garment 102 has been configured to fit inside the second pocket 170, the body portion 110 may be flipped or pivoted about the pivot point 182 or connection between the body portion 110 and the second pocket 170, as indicated by arrows F in FIG. 10. The pivot point 182 may be arranged at a top end of the second pocket 170, and preferably at or adjacent to the bottom edge 139 of the waistband 138. The second pocket 170 may be deformed, and the elastic strip 180 stretched, to widen or open the top opening 172, as indicated by arrow G, and allow the body portion 110 to further pivot over and into the top opening 172 as indicated by arrow H in FIG. 11, and further into the interior space 174 of the second pocket 170. Once the body portion 110 has been received in the interior space 174 of the second pocket 170, the elastic strip 180 may be relaxed and elastically compressed against the body portion 110, as indicated by arrows I in FIG. 11, securing the body portion 110 within the interior space 174. In this final or stowage position of the body portion 110, shown in front view in FIG. 12, the soiled body portion 110 is fluid-tightly received within the interior space 174 of the second pocket 170 such that any fluids emanating from the body portion 110 are retained within the interior space 174 by the fluid-tight second pocket 170 and elastic strip 180. The collapsed and stowed undergarment 102 shown in FIG. 12 may be hygienically and discreetly transported until further processing.

The present invention therefore allows a wearer to store supplies such as, but not limited to, portable catheters, wipes, pads, liners, and disposable underwear, in a concealed location of the underwear garment while maintaining the wearer's privacy. The user may carry these items without any telltale signs showing through clothing, which may alert others of the wearer's medical impairments. In addition, stored supplies can be removed from the pockets discreetly by the wearer reaching just inside the waistband to remove an item from the undergarment within the pockets. In turn, the fluid-tight, second pocket allows the wearer to privately and securely replace the soiled underwear garment with a clean underwear garment, which may be obtained from the first or second pocket, and rapidly and discreetly store the soiled underwear in the second pocket, without nearby persons becoming aware of the occurrence.

In summary, the present invention provides an underwear garment which contains effectively concealed and secured pockets, including a personal item storage pocket for carrying medical supplies, personal items, etc., and an impermeable pocket providing an easy and effective means of storing soiled underwear. The pockets may also provide for the storage of a clean replacement underwear. In this way, the invention provides a novel, unique, holistic, sustainable, and non-invasive remedy for people suffering from urological (incontinence, MS, etc.), intestinal conditions (i.e. Crohn's disease, etc.), or other medical conditions to store their medications, medical supplies, clean replacement underwear and soiled underwear, in a discreet, hygienic and helpful manner.

Alternative embodiments are contemplated without departing from the scope of the present disclosure. For example, the invention is not limited in form to the number of different materials that can be utilized to create the invention and/or articles of fabric clothing that can be used simultaneously at any one time and/or the shape of human clothing and/or pockets, as they could take just about any other shape imaginable.

Since many modifications, variations, and changes in detail can be made to the described preferred embodiments of the invention, it is intended that all matters in the foregoing description and shown in the accompanying drawings be interpreted as illustrative and not in a limiting sense. Furthermore, it is understood that any of the features presented in the embodiments may be integrated into any of the other embodiments unless explicitly stated otherwise. The scope of the invention should be determined by the appended claims and their legal equivalents.

What is claimed is:

1. An underwear garment system comprising:
    a main underwear garment, the main underwear garment comprising:
        a body portion configured to be worn about a trunk of a wearer, predominantly below a waist of the wearer and along a crotch area of the wearer, the body portion comprising an inner side configured to face the wearer, and
        a first pocket and a second pocket carried by the body portion on the inner side thereof, the first pocket and second pocket comprising a respective top opening providing access to a respective interior space, wherein
        the second pocket is formed of a fluid impermeable material and is suspended from the body portion such that a connection between the second pocket and body portion defines a pivot point, wherein the body portion is deformable and pivotable about the pivot point to fit within the interior space of the second pocket; wherein the main underwear garment is configured to selectively adopt:
 a first configuration, in which the body portion is deployed and wearable by the wearer, and the first and second pockets are arranged on the inner side of the body portion and concealed from an outside observer, and
 a second configuration, in which the body portion is deformed to fit within the interior space of the second pocket, and is pivoted about the pivot point and received within the interior space of the second pocket, and further in which the second pocket prevents a fluid emanating from the body portion from leaking out of the interior space of the second pocket; and
a second underwear garment, wherein the second underwear garment is deformable and fittable through the top opening of the first pocket and within the interior space of the first pocket.

2. The underwear garment system of claim 1, wherein the main underwear garment comprises a waistband at a top edge of the body portion, and further wherein the opening of the first pocket is arranged adjacent to the waistband.

3. The underwear garment system of claim 2, wherein the opening of the first pocket is arranged at a bottom edge of the waistband.

4. The underwear garment system of claim 1, wherein the main underwear garment comprises at least one waistband at a top edge of the body portion, and further wherein the opening of the second pocket is arranged adjacent to the waistband.

5. The underwear garment system of claim 4, wherein the opening of the second pocket is arranged at a bottom edge of the waistband.

6. The underwear garment system of claim 1, wherein the main underwear garment comprises at least one waistband at a top edge of the body portion, and further wherein the openings of the first and second pockets are arranged adjacent to the waistband.

7. The underwear garment system of claim 6, wherein the openings of the first and second pockets are arranged at a bottom edge of the waistband.

8. The underwear garment system of claim 1, wherein the first and second pockets are elongated along a left-to-right direction of the underwear garment.

9. The underwear garment system of claim 1, wherein the first pocket, top opening of the first pocket, and interior space of the first pocket are defined by and between the inner side of the body portion and a panel attached to the inner side of the body portion.

10. The underwear garment system of claim 1, wherein the second pocket is defined by first and second panels extending from one another at a bottom edge and opposite side edges, wherein the top opening of the second pocket is defined by and between respective top edges of the first and second panels.

11. The underwear garment system of claim 1, wherein the second pocket comprises an elastic strip at the top opening of the second pocket, and further wherein, in the second configuration of the main underwear garment, the elastic strip is compressed to thereby retain the body portion within the interior space of the second pocket.

12. The underwear garment system of claim 11, wherein the elastic strip surrounds the top opening of the second pocket in its entirety.

13. The underwear garment system of claim 11, wherein, in the first configuration of the main underwear garment, the elastic strip is stretched and tensioned.

14. The underwear garment system of claim 1, wherein the second underwear garment is made of a single fabric layer.

15. The underwear garment system of claim 1, further comprising a second underwear garment, wherein the second underwear garment is deformable and fittable through the top opening of the second pocket and within the interior space of the second pocket.

16. The underwear garment system of claim 15, wherein the second underwear garment is made of a single fabric layer.

17. The underwear garment system of claim 1, wherein at least one of the first and second pockets is non-detachably attached to the body portion.

18. An underwear garment system comprising:
a main underwear garment, the main underwear garment comprising:
 a body portion configured to be worn about a trunk of a wearer, predominantly below a waist of the wearer and along a crotch area of the wearer, the body portion comprising an inner side configured to face the wearer,
 a waistband arranged at a top edge of the body portion, and
 a first pocket and a second pocket carried by the body portion on the inner side thereof, the first pocket and second pocket comprising a respective top opening arranged adjacent to the waistband and providing access to a respective interior space, wherein
the second pocket is formed of a fluid impermeable material and is suspended from the body portion such that a connection between the second pocket and body portion defines a pivot point, the second pocket comprising an elastic strip at the top opening of the second pocket, wherein
the body portion is deformable and pivotable about the pivot point to fit within the interior space of the second pocket; wherein
the main underwear garment is configured to selectively adopt:
 a first configuration, in which the body portion is deployed and wearable by the wearer, and the first and second pockets are arranged on the inner side of the body portion and concealed from an outside observer, and
 a second configuration, in which the body portion is deformed to fit within the interior space of the second pocket, and is pivoted about the pivot point and received within the interior space of the second pocket, and the elastic strip is compressed to thereby retain the body portion within the interior space of the second pocket, and further in which the second pocket prevents a fluid emanating from the body portion from leaking out of the interior space of the second pocket; and
a second underwear garment, wherein the second underwear garment is deformable and fittable through the top opening of the first pocket and within the interior space of the first pocket.

19. An underwear garment system comprising:
a main underwear garment, the main underwear garment comprising:
   a body portion configured to be worn about a trunk of a wearer, predominantly below a waist of the wearer and along a crotch area of the wearer, the body portion comprising an inner side configured to face the wearer,
   a waistband arranged at a top edge of the body portion, and
   a first pocket and a second pocket carried by the body portion on the inner side thereof, the first pocket and second pocket comprising a respective top opening arranged adjacent to the waistband and providing access to a respective interior space, wherein
   the second pocket is formed of a fluid impermeable material and is suspended from the body portion such that a connection between the second pocket and body portion defines a pivot point, the second pocket comprising an elastic strip at the top opening of the second pocket, wherein
   the body portion is deformable and pivotable about the pivot point to fit within the interior space of the second pocket; and
   a second underwear garment, wherein the second underwear garment is deformable and fittable through the top opening of at least one of the first pocket and the second pocket and within the interior space of said at least one of the first pocket and the second pocket; wherein
the main underwear garment is configured to selectively adopt:
   a first configuration, in which the body portion is deployed and wearable by the wearer, and the first and second pockets are arranged on the inner side of the body portion and concealed from an outside observer, and further in which the second underwear garment is deformed, received and concealed within one of the first and second pockets, and
   a second configuration, in which the body portion is deformed to fit within the interior space of the second pocket, and is pivoted about the pivot point and received within the interior space of the second pocket, and the elastic strip is compressed to thereby retain the body portion within the interior space of the second pocket, and further in which the second pocket prevents a fluid emanating from the body portion from leaking out of the interior space of the second pocket.

\* \* \* \* \*